(12) United States Patent
Hedrick et al.

(10) Patent No.: US 10,117,966 B2
(45) Date of Patent: *Nov. 6, 2018

(54) METHOD FOR PRODUCING NANOSURFACES WITH NANO, MICRON, AND/OR SUBMICRON STRUCTURES ON A POLYMER

(71) Applicant: NANOVIS, INC., West Lafayette, IN (US)

(72) Inventors: Matthew Hedrick, Carmel, IN (US); Ganesan Balasundaram, Minneapolis, MN (US); Chang Yao, West Lafayette, IN (US)

(73) Assignee: NANOVIS, INC., Columbia City, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,747

(22) Filed: Mar. 10, 2016

(65) Prior Publication Data

US 2016/0325014 A1 Nov. 10, 2016

Related U.S. Application Data

(63) Continuation of application No. 13/704,735, filed as application No. PCT/US2011/041490 on Jun. 22, 2011, now Pat. No. 9,393,092.
(Continued)

(51) Int. Cl.
*A61L 27/18* (2006.01)
*A61L 17/04* (2006.01)
(Continued)

(52) U.S. Cl.
CPC .......... *A61L 27/18* (2013.01); *A61B 17/0401* (2013.01); *A61B 17/06166* (2013.01);
(Continued)

(58) Field of Classification Search
CPC ....................................................... A61L 27/18
(Continued)

(56) References Cited

U.S. PATENT DOCUMENTS 3,287,322 A 11/1966 Zimmer et al.
6,248,129 B1 6/2001 Froix
(Continued)

FOREIGN PATENT DOCUMENTS

JP 2005281679 A 10/2005
KR 1020090088224 A 8/2009
(Continued)

OTHER PUBLICATIONS

International Search Report and Written Opinion issued in PCT/US2011/041490, dated Mar. 6, 2012.
(Continued)

*Primary Examiner* — Dah-Wei D Yuan
*Assistant Examiner* — Andrew Bowman
(74) *Attorney, Agent, or Firm* — Heslin Rothenberg Farley & Mesiti P.C.

(57) ABSTRACT

The present invention relates to a modified polymeric material. The modified polymeric material includes a polymer having a modified surface, where the modified surface includes nano, micron, and/or submicron scale features. The present invention also relates to an implant comprising the modified polymeric material. The present invention further relates to processes for making the modified polymeric material and the implant.

19 Claims, 15 Drawing Sheets

1. Heat (Pre-set) + High Vacuum (~10⁻⁵ torr)
2. Methylene Chloride Treatment + High Vacuum (~10⁻⁶ torr)

Schematics of Surface Modified Nanopolypropylene

Related U.S. Application Data

(60) Provisional application No. 61/358,851, filed on Jun. 25, 2010.

(51) Int. Cl.

| | | |
|---|---|---|
| *A61L 17/14* | (2006.01) |
| *A61L 27/50* | (2006.01) |
| *A61L 31/04* | (2006.01) |
| *A61L 31/06* | (2006.01) |
| *A61L 31/14* | (2006.01) |
| *C08G 63/88* | (2006.01) |
| *C08L 71/00* | (2006.01) |
| *A61B 17/04* | (2006.01) |
| *A61B 17/06* | (2006.01) |
| *A61C 8/00* | (2006.01) |
| *A61F 2/00* | (2006.01) |
| *A61L 27/10* | (2006.01) |
| *B29C 59/02* | (2006.01) |
| *C08F 110/06* | (2006.01) |
| *C08G 65/40* | (2006.01) |
| *C08G 65/46* | (2006.01) |
| *B29C 41/24* | (2006.01) |
| *B29K 71/00* | (2006.01) |
| *B29L 31/00* | (2006.01) |

(52) U.S. Cl.
CPC .............. *A61C 8/00* (2013.01); *A61F 2/0063* (2013.01); *A61L 17/04* (2013.01); *A61L 17/14* (2013.01); *A61L 27/10* (2013.01); *A61L 27/50* (2013.01); *A61L 31/048* (2013.01); *A61L 31/06* (2013.01); *A61L 31/14* (2013.01); *B29C 59/022* (2013.01); *C08F 110/06* (2013.01); *C08G 63/88* (2013.01); *C08G 65/4012* (2013.01); *C08G 65/46* (2013.01); *C08L 71/00* (2013.01); *A61L 2400/12* (2013.01); *A61L 2400/18* (2013.01); *B29C 41/24* (2013.01); *B29K 2071/00* (2013.01); *B29L 2031/7532* (2013.01); *C08G 2650/40* (2013.01); *Y10T 428/24355* (2015.01); *Y10T 428/2978* (2015.01); *Y10T 428/2982* (2015.01)

(58) Field of Classification Search
USPC .......................................................... 427/2.1
See application file for complete search history.

(56) References Cited

U.S. PATENT DOCUMENTS

| | | |
|---|---|---|
| 6,258,335 B1 | 7/2001 | Bhattacharya |
| 7,138,180 B2 | 11/2006 | Denes et al. |
| 9,393,092 B2 * | 7/2016 | Balasundaram ........ A61L 17/04 |
| 2006/0147492 A1 | 7/2006 | Hunter et al. |
| 2006/0208390 A1 | 9/2006 | Charbonneaux et al. |
| 2007/0259427 A1 | 11/2007 | Storey et al. |
| 2010/0168506 A1 | 7/2010 | Moon et al. |
| 2013/0330688 A1 | 12/2013 | Hedrick et al. |

FOREIGN PATENT DOCUMENTS

| | | |
|---|---|---|
| WO | 2009149827 A1 | 12/2009 |
| WO | 2011163393 A2 | 12/2011 |

OTHER PUBLICATIONS

Hasegawa, M., et al., Low-CTE Polyimides Derived from 2,3,6,7-Naphthalenetetracarboxylic Dianhydride, Polymer Journal, vol. 39, No. 6, pp. 610-621 (2007).

Extended European Search Report, Supplementary European Search Report, and European search opinion issued by the European Patent Office for application No. EP11798868.3 dated Jul. 20, 2016.

* cited by examiner

SEM images of Surface Modified Nano PEEK

High magnification SEM images of surface modified nano PEEK

EDS spectra of nano and conventional PEEK.

Heat + vacuum treated PEEK Calcium deposition data with osteoblast cell.

1. Heat (Pre-set) + High Vacuum (~$10^{-6}$ torr)
2. Methylene Chloride Treatment + High Vacuum (~$10^{-6}$ torr)
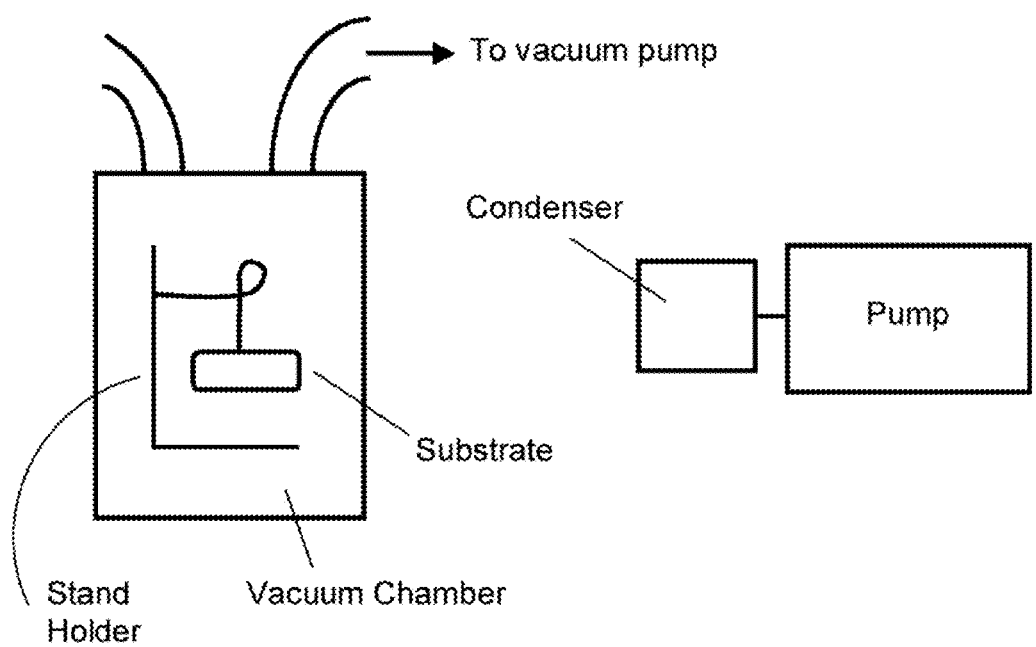
Schematics of Surface Modified Nanopolypropylene
FIG. 6

Plain

Methylene chloride treatment with high vacuum process

Pre-set low heat with high vacuum process

SEM of Polypropylene mesh. Note the obvious nano features with treated samples.

METHOD FOR PRODUCING NANOSURFACES WITH NANO, MICRON, AND/OR SUBMICRON STRUCTURES ON A POLYMER

CROSS-REFERENCE TO RELATED APPLICATIONS

This application is a continuation application of U.S. application Ser. No. 13/704,735, filed with the U.S. Patent and Trademark Office on Jul. 25, 2013, which is a national stage filing under section 371 of International Application No. PCT/US2011/041490, filed on Jun. 22, 2011, and published in English on Dec. 29, 2011 as WO 2011/163393, which claims the benefit of U.S. Provisional Patent Application Ser. No. 61/358,851, filed Jun. 25, 2010, the entire disclosure of which is incorporated by reference herein.

FIELD OF THE INVENTION

The present invention relates to a modified polymeric material. The present invention also relates to an implant comprising the modified polymeric material. The present invention further relates to processes for making and using the modified polymeric material and the implant.

BACKGROUND OF THE INVENTION

There is an interest in the potential use of synthetic polymers and the effect they may have on the design and function of hard and soft tissue repair. To that end, various nanotechnology-based approaches have been taken.

However, current methods for creating a surface roughness (e.g., at the submicron and micron level) are deficient in terms of scaling, cost, complexity, reagent acquisition, disposal, and accessibility, biocompatibility, and mechanical properties of the substrate.

Other deficiencies in the art of producing synthetic polymers having rough surfaces at the nano, submicron, and micron level include, for example, the following: (i) current methods to create nanosurface roughness on polymers are difficult in maintaining consistency across the material type; (ii) current methods to create nanosurface roughness on polymers use chemicals that are potentially toxic if such chemicals are not completely removed; (iii) current methods to create nanosurface roughness on polymers use coating methods that can result in delamination of the polymer or added material and wear debris formation; (iv) current methods to create nanosurface roughness on polymers are difficult to apply in three dimensions/outside of direct line of site; and (v) current methods have difficulty creating both porous voids and aspirities.

The present invention is directed to overcoming these and other deficiencies in the art.

SUMMARY OF THE INVENTION

In one aspect, the present invention relates to a modified polymeric material, as described herein. In one embodiment, the modified polymeric material of the present invention includes a polymer having a modified surface, where the modified surface includes nano, micron, and/or submicron scale features, including, but not limited to, pores, peaks, valleys, and ridges.

In another aspect, the present invention relates to an implant that includes a modified polymeric material, as described herein.

In a further aspect, the present invention relates to a process for preparing a modified polymeric material, as described herein.

In one embodiment, the process involves providing a polymer, and subjecting the polymer to a high vacuum treatment regimen under conditions effective to modify the surface of the polymer by introducing nano, micron, and/or submicron scale features to the surface of the polymer. The high vacuum treatment regimen can include heating the polymer at a high temperature, and then incubating the heat-treated polymer in a vacuum chamber under high vacuum conditions effective to modify the surface of the polymer.

In another embodiment, the process involves providing a polymer, and incubating the polymer in mild heat in a vacuum chamber under high vacuum conditions effective to modify the surface of the polymer by introducing nano, micron, and/or submicron scale features to the surface of the polymer.

In yet another embodiment, the process involves providing a polymer, treating the polymer with a chemical, enzyme, or other agent to soften the surface, and then subjecting the polymer to vacuum conditions effective to modify the surface of the polymer by introducing nano, micron, and/or submicron scale features to the surface of the polymer.

In yet another embodiment, the process involves providing a polymer, and incubating the polymer in methylene chloride, or other chemical, pharmaceutical, biologic agent, antibiotics, antimicrobial or bacterial static metals or other agents, growth factors, peptides, antibodies, viruses, RNAi, ceramic including but not limited to hydroxyapatite and calcium phosphate in all size ranges, metal including but not limited to titanium, Ti6Al4V, or another polymer in a vacuum chamber under high vacuum conditions effective to modify the surface of the polymer by introducing nano, micron, and/or submicron scale features to the surface of the polymer and coat or integrate the chemical, pharmaceutical, antibiotic, antimicrobial or bacterio-static metal or other agent, biologic agent, growth factors, peptides, antibodies, virus, RNAi, ceramic, metal or another polymer to the polymer.

Alternatively, the polymer could have the above agents in the polymer prior to the process.

In another aspect, the present invention relates to a modified polymeric material produced according to the processes described herein, as well as to implants containing the modified polymeric material.

The present invention provides a robust method for producing nanosurfaces and nanosurfaces with nano, submicron, and micron scale features on polymers, including nanosurfaced polyetheretherketone (PEEK) spine cages and nanosurfaced polypropylene hernia meshes, polymer sutures and various polymers, including those used for implants, biomaterials, or drug delivery materials in any type of human or animal tissue.

The modified polymeric material of the present invention can be used for both hard and soft tissue repair. In one aspect, the invention is effective in developing nano-PEEK spine cages to treat spine repair and other applications that use PEEK polymer. Additionally, the invention provides nanosurfaced polypropylene hernia meshes. The invention further provides an inexpensive and consistent process that creates a nanosurface on polymers with a 2 or 3 dimensional geometry. The process of the present invention is useful in that it is easily scalable, does not use chemicals, and preserves the biocompatibility and mechanical properties of the substrate material. Furthermore the nanosurface of the modified polymeric material of the present invention can be useful in improving or modifying biological responses, including protein or antibody adsorption, cell attachment, cell function, and subsequent tissue growth. The surface of the modified polymeric material of the present invention can also improve therapeutic attachment and delivery of various attachments, including, for example, peptides, proteins, antibodies, drugs, metals, antimicrobial metals, biologic tissues or agents, stem cells, modified cells, and the like.

The present invention also provides PEEK and polypropylene surfaces that mimic natural tissues, and that may be more bioactive and, thus, provide improved hard and soft tissue integration markers compared to conventional PEEK and polypropylene surfaces. As mentioned, the present invention provides a nano to nano and micron rough surface.

With regard to biomedical uses, currently existing conventional PEEK materials to treat spine repair possess smooth material surface features. The same trend applies to polypropylene based materials that are widely used in hernia repair applications. Therefore, nano rough surface modification of such polymeric materials, as provided by the present invention, is a new paradigm for quick repair and surrounding tissue integration.

The present invention provides, in one aspect, a process for preparing a modified polymeric material using simultaneous heat and vacuum treatment on PEEK polymeric material (without chemical process) to create nano rough surface without compromising the mechanical, physical and chemical property of the polymer.

For polypropylene hernia meshes, the present invention provides, in one aspect, a method that uses a high vacuum source in the presence of pre-set mild heat or highly volatile methylene chloride treatment. The methylene chloride has a very low boiling point (less than 40° C.; close to body temperature heat) and can be removed spontaneously during the high vacuum treatment.

The present invention also relates to incorporating the process for preparing a modified polymeric material into the PEEK manufacturing process. This modified process can be useful for creating a surface or pores in polymers (such as when the polymer is molded/extruded for the first time).

The present invention also relates to using the process for preparing a modified polymeric material to surfaces that are already modified or will be modified thereafter. For example, the present invention contemplates using the modified process of the present invention to the top of a previously modified surface, and also contemplates using another method (e.g., acid etching) to further modify the modified surface after the process for preparing the modified polymeric material to the surface is completed.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 6 are schematics of one embodiment of the process of preparing a surface modified nanopolypropylene of the present invention.

FIG. 7B shows an SEM image of the surface a nanopolypropylene mesh produced using methylene chloride treatment with high vacuum. FIG. 7C shows an SEM image of the surface a nanopolypropylene mesh produced using pre-set heat with high vacuum.

DETAILED DESCRIPTION OF THE INVENTION

Figure 1:
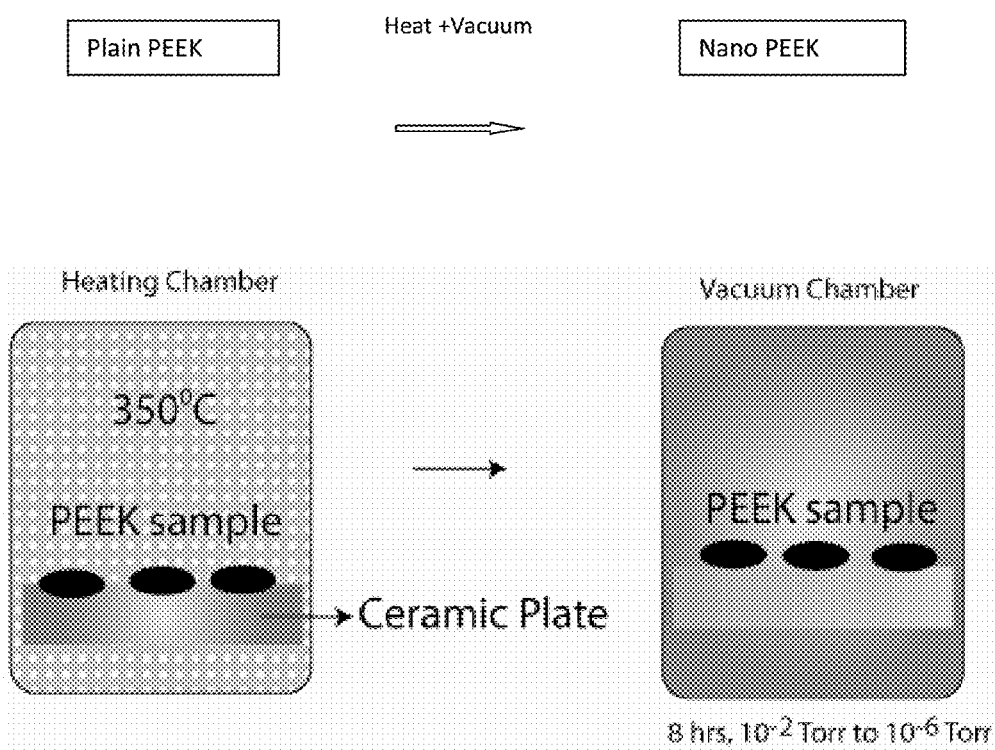
FIG. 1 is a schematic of one embodiment of the process of the present invention for preparing a modified polymeric material. In this embodiment, the process produces a nano PEEK modified polymeric material.

The present invention relates to a modified polymeric material, as described herein. In one embodiment, the modified polymeric material of the present invention includes a polymer having a modified surface, where the modified surface includes nano, micron, and/or submicron scale features. In one embodiment, the nano, micron, and/or submicron scale features can include, without limitation, surface features such as pores, peaks, valleys, and ridges.

A suitable polymer can include, without limitation, a thermoplastic polymer. Examples of such thermoplastic polymers include polypropylene, polyetheretherketone (PEEK), poly lactic glycolic acid, poly lactic lactic acid, poly lactic acid, polyurethane, and the like. In one embodiment, the polymer is in the form of a polymeric film. In other embodiments, the polymer is in the form of a fiber, sphere, ovoid, rod, filament, monofilament, scaffold, plug, matrix, or the like.

The modified polymeric material of the present invention can be effective to modify biological response (e.g., increased or decreased tissue or bacteria attachment), fixation (e.g., improve mechanical interface with bone), or therapeutic attachment/delivery compared to a corresponding non-modified polymeric material.

The modified polymeric material of the present invention can be effective to increase biological response or therapeutic attachment/delivery compared to a corresponding non-modified polymeric material. Examples of biological responses contemplated by the present invention include, without limitation, protein or antibody adsorption, cell attachment, cell function, tissue growth, and the like. Examples of therapeutics contemplated by the present invention include, without limitation, peptides, proteins, growth factors, antibodies, drugs, metals, antimicrobial metals, biologic tissues, biologic agents, stem cells, modified cells, and the like, including various others materials such as, but not limited to, various ceramics (e.g., HA, CP, etc.) and metals (e.g., Ti, etc.).

The present invention further includes treating the modified polymeric material with a plasma treatment in an atmosphere including, but not limited to, an oxygen atmosphere, plasma etching, oxygenation, or plasma spraying with a ceramic, adding allograft, Demineralized bone matrix, or xenograft.

Therefore, in one embodiment, the modified polymeric material of the present invention can further include a functional attachment effective to increase biological response or therapeutic attachment/delivery. The functional attachment can include, without limitation, a peptide, protein, growth factor, antibody, drug, metal, antimicrobial metal, biologic tissue, biologic agent, chemical agent, stem cell, modified cell, and the like.

In a further embodiment, the modified polymeric material of the present invention can further include: (i) a functional attachment effective to increase biological response or therapeutic attachment/delivery; and/or (ii) a ceramic, metal, or another polymer integrated into the modified polymeric material or coated onto the surface of the modified polymeric material.

The present invention also relates to an implant that includes a modified polymeric material, as described herein. In one embodiment, the thermoplastic polymer is polypropylene and the implant is a hernia mesh or polymer suture. In another embodiment, the thermoplastic polymer is PEEK and the implant is a spine cage, vertebral body replacement, suture anchor, dental implant, or maxillofacial implant, and the like.

The present invention further relates to a process for preparing a modified polymeric material, as described herein.

In one embodiment, the process involves: (i) providing a polymer; and (ii) subjecting the polymer to a high vacuum treatment regimen under conditions effective to modify the surface of the polymer by introducing nano, micron, and/or submicron scale features to the surface of the polymer. In a particular embodiment of this process, the high vacuum treatment regimen can include: (i) heating the polymer at a high temperature; and (ii) incubating the heat-treated polymer in a vacuum chamber under high vacuum conditions effective to modify the surface of the polymer. The polymer used in this embodiment of the process of the present invention can include, without limitation, PEEK.

The heating can be at a heat range specific to the polymer and relative to the polymer's melting and crystallization temperature. The incubating can be carried out for at least 5 hours.

In illustrative examples, the heating can be carried out at a temperature of greater than 400° C., between about 275° C. and about 400° C., between about 300° C. and about 400° C., between about 325° C. and about 400° C., between about 350° C. and about 400° C., or between about 375° C. and about 400° C. In a particular embodiment, the heating can be carried out at a temperature of about 350° C. for between about 1 and about 90 minutes. The material can be heated and vacuum treated simultaneously. The heating and simultaneous high vacuum conditions are such as to be effective to modify the surface of the polymer in accordance with the present invention. The temperature and vaccum pressure can be modified to create different surface features to achieve the desired biological response or other response or benefit.

In a variation of this embodiment, the high vacuum treatment regimen can include loading polymer samples at 150° C. and subjecting the polymer to pump-down procedures to 10 mTorr (pump/purge sequences). Thereafter, the polymer is subjected to a ramp-up period during which the temperature is increased from about 150° C. to about 350° C. over the course of approximately 1 hour. The polymer is left at steady state for about 1 hour (at 10 mTorr at 350° C.). The polymer is then subjected to a ramp-down period during which the temperature is decreased to about 150° C. over the course of 1 hour. The sample is then extracted at 150° C. and transferred to a vacuum desiccator and stored under high vacuum for approximately 8 hours.

Figure 15A:
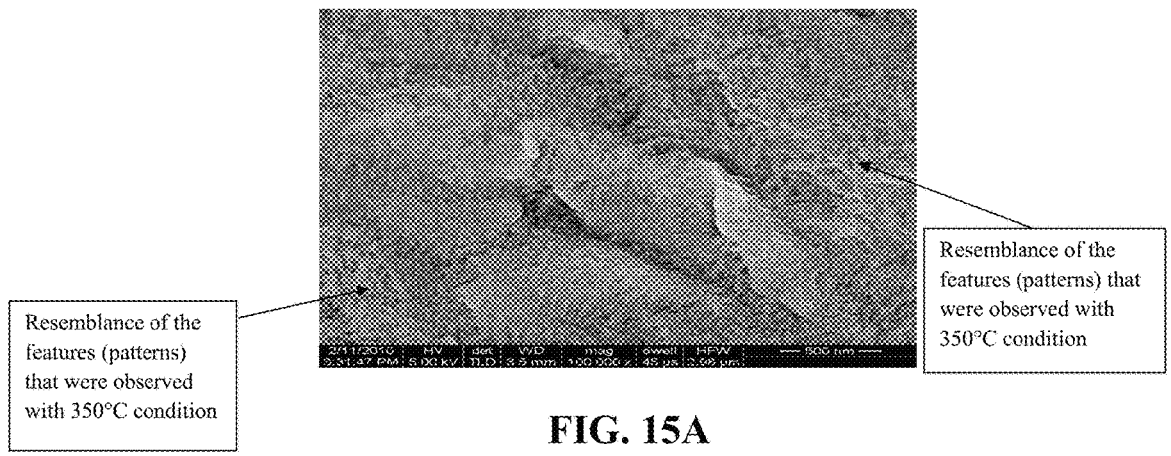
FIGS. 15A-15B are SEM images of the surface of a modified PEEK material produced using an embodiment of the process of the present invention involving heating at 275° C. using a ramping protocol. Arrows indicate the resemblance of the features (patterns) that were observed with 350° C. condition.
Figure 15B:
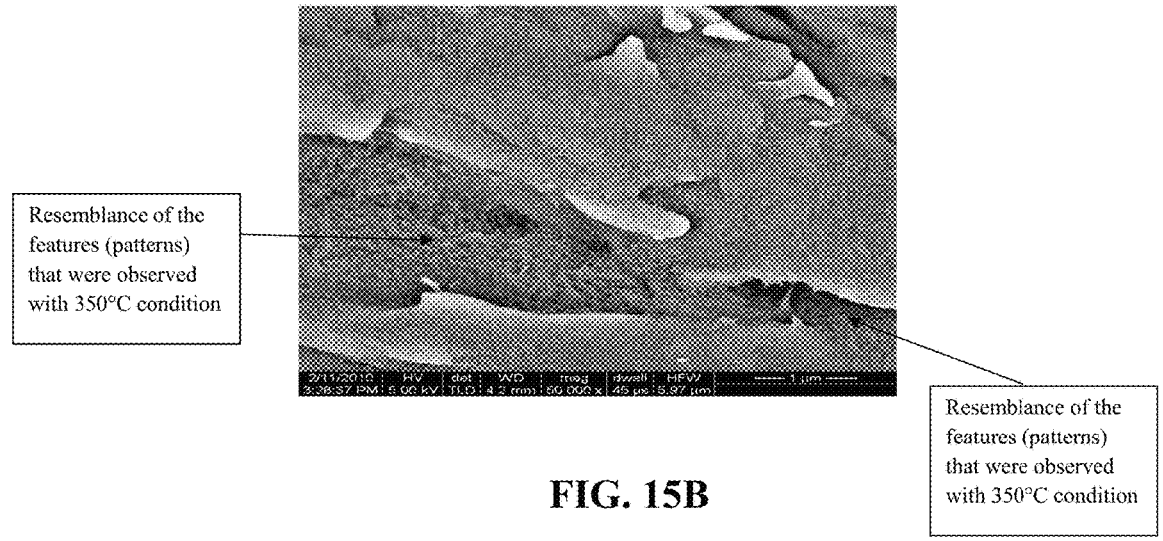

In another embodiment, the process involves heating at 275° C. using a ramping protocol, same as for 350° C. Other conditions of the process can be the same, but the maximum temperature can be held at 275° C. for 1 hour. Surface features of a modified polymeric material produced using such process are shown in FIGS. 15A-15B. For example, as shown in FIGS. 15A-15B, the SEM results provided a new type of surface feature in this condition. In particular, the topography is rougher but with less porous structure compared to 350° C. treatment condition. Again the topographical features were homogenous throughout the surface like the 350° C. treatment.

In one aspect, the process of the present invention is effective to produce a modified polymeric material that includes a polymer having a modified surface, where the modified surface includes micron and/or submicron scale features. In one embodiment, the polymer is a thermoplastic polymer, where the thermoplastic polymer includes, but is not limited to, polypropylene and polyetheretherketone (PEEK). In a particular embodiment, the polymer is in the form of a polymeric film. In another embodiment, the modified polymeric material is effective to increase biological response or therapeutic attachment/delivery compared to a corresponding non-modified polymeric material. The biological response can include, without limitation, protein or antibody adsorption, cell attachment, cell function, and tissue growth. The therapeutic can be, without limitation, a peptide, protein, growth factor, antibody, drug, metal, antimicrobial metal, biologic tissue, biologic agent, chemical agent, stem cell, modified cell, and the like. Further, the modified polymeric material can further include a functional attachment effective to increase biological response or therapeutic attachment/delivery. Suitable functional attachments can include, without limitation, a peptide, protein, growth factor, antibody, drug, metal, antimicrobial metal, biologic tissue, biologic agent, chemical agent, stem cell, modified cell, and the like.

In one embodiment, the process of preparing a modified polymeric material can further include: (i) applying an acid etching procedure either before or after the polymer is modified; and/or (ii) integrating/coating the modified polymeric material with hydroxyapatite, titanium, calcium phosphate, and/or the like to yield a two layer or integration of the modified polymeric material and the hydroxyapatite, titanium, calcium phosphate, and the like.

In another embodiment, the process involves: (i) providing a polymer; and (ii) incubating the polymer in mild heat in a vacuum chamber under high vacuum conditions effective to modify the surface of the polymer by introducing micron and/or submicron scale features to the surface of the polymer. The polymer used in this embodiment of the process of the present invention can include, without limitation, polypropylene. The mild heat can be, without limitation, a temperature of not more than about 70° C. The incubating can be carried out for between about 18 and 30 hours.

In yet another embodiment, the process involves: (i) providing a polymer; and (ii) incubating the polymer in methylene chloride in a vacuum chamber under high vacuum conditions effective to modify the surface of the polymer by introducing micron and/or submicron scale features to the surface of the polymer. The polymer used in this embodiment of the process of the present invention can include, without limitation, polypropylene. The incubating can be carried out for between about 18 and 30 hours.

In another aspect, the present invention relates to a modified polymeric material produced according to the processes described herein, as well as to implants containing the modified polymeric material. In view of the present disclosure, one of ordinary skill in the art would readily be able to prepare and use implants that contain or include the modified polymeric material of the present invention.

In another aspect, the present invention relates to using the modified polymeric material of the present invention as or combined with various biomaterials (e.g., scaffolds, bone void fillers, fusion materials autograft, Demineralized bone graft, allograft, xenograft, and the like), components, local and systemic drug delivery materials/polymers, and various other items suitable for being used or combined with the modified polymeric material.

In another aspect, the present invention provides a modified polymeric material that further includes two layer/integration aspects (e.g., integrating/coating with hydroxyapatite, titanium, calcium phosphate).

One advantage of the present invention is the straightforward creation of novel nanosurfaced polymers for spinal repair, spinal fusion, dental implants, biomaterials, suture anchors, and where other alternatives are not possible, including in porous structures that are hard to reach with fluids or line of site methods. The method of the present invention involves no chemical treatment or cumbersome coating technologies traditionally used in polymer surface modifications that attempt to create a nano rough surface. The procedure of the present invention is easy and cost effective, efficient for mass production; in particular there will be no chemical residues and reduced particle debris. Further, no major bulk mechanical property will be changed since the processing temperature involves is low compared to the melting temperature of the polymer.

As noted herein, the present invention precludes the usage of chemical treatment, which is a concern that needs to be addressed in the context of cytotoxicity. Also, conventionally used coating technologies (to create nano, micron, or submicron roughness) possibly produce delamination or wear debris, which results in the potential for cytotoxicity. The present invention also provides a method to create a custom nanosurface to drive desired protein/antibody adsorption and cell responses. For example, this could be done by changing the process parameters to make a different nano and micron surfaces.

Provided below are further descriptions of certain aspects and embodiments of the present invention, some descriptions of which reiterate or further explain various aspects and embodiments contained elsewhere herein.

In one embodiment, the process of the present invention involves providing a polymer, and subjecting the polymer to a high vacuum treatment regimen under conditions effective to modify the surface of the polymer by introducing nano, micron, and/or submicron scale features to the surface of the polymer. The high vacuum treatment regimen can include heating the polymer at a high temperature, and then incubating the heat-treated polymer in a vacuum chamber under high vacuum conditions effective to modify the surface of the polymer.

In another embodiment, the process involves providing a polymer, and incubating the polymer in mild heat in a vacuum chamber under high vacuum conditions effective to modify the surface of the polymer by introducing nano, micron, and/or submicron scale features to the surface of the polymer.

In yet another embodiment, the process involves providing a polymer, treating the polymer with a chemical, enzyme, or other agent to soften the surface, and then subjecting the polymer to vacuum conditions effective to modify the surface of the polymer by introducing nano, micron, and/or submicron scale features to the surface of the polymer.

In yet another embodiment, the process involves providing a polymer, and incubating the polymer in methylene chloride, or other chemical, pharmaceutical, biologic agent, antibiotics, antimicrobial or bacterial static metals or other agents, growth factors, peptides, antibodies, viruses, RNAi, ceramic including but not limited to hydroxyapatite and calcium phosphate in all size ranges, metal including but not limited to titanium, Ti6Al4V, or another polymer in a vacuum chamber under high vacuum conditions effective to modify the surface of the polymer by introducing nano, micron, and/or submicron scale features to the surface of the polymer and coat or integrate the chemical, pharmaceutical, antibiotic, antimicrobial or bacterio-static metal or other agent, biologic agent, growth factors, peptides, antibodies, virus, RNAi, ceramic, metal or another polymer to the polymer.

Alternatively, the polymer could have the above agents in the polymer prior to the process.

In another aspect, the present invention relates to a modified polymeric material produced according to the processes described herein, as well as to implants containing the modified polymeric material.

The present invention provides a robust method for producing nanosurfaces and nanosurfaces with nano, submicron, and micron scale features on polymers, including nanosurfaced polyetheretherketone (PEEK) spine cages and nanosurfaced polypropylene hernia meshes, polymer sutures and various polymers, including those used for implants, biomaterials, or drug delivery materials in any type of human or animal tissue.

The modified polymeric material of the present invention can be used for both hard and soft tissue repair. In one aspect, the invention is effective in developing nano-PEEK spine cages to treat spine repair and other applications that use PEEK polymer. Additionally, the invention provides nanosurfaced polypropylene hernia meshes. The invention further provides an inexpensive and consistent process that creates a nanosurface on polymers with a 2 or 3 dimensional geometry. The process of the present invention is useful in that it is easily scalable, does not use chemicals, and preserves the biocompatibility and mechanical properties of the substrate material. Furthermore the nanosurface of the modified polymeric material of the present invention can be useful in improving or modifying biological responses, including protein or antibody adsorption, cell attachment, cell function, and subsequent tissue growth. The surface of the modified polymeric material of the present invention can also improve therapeutic attachment and delivery of various attachments, including, for example, peptides, proteins, antibodies, drugs, metals, antimicrobial metals, biologic tissues or agents, stem cells, modified cells, and the like.

The present invention also provides PEEK and polypropylene surfaces that mimic natural tissues, and that may be more bioactive and, thus, provide improved hard and soft tissue integration markers compared to conventional PEEK and polypropylene surfaces. As mentioned, the present invention provides a nano to nano and micron rough surface.

With regard to biomedical uses, currently existing conventional PEEK materials to treat spine repair possess smooth material surface features. The same trend applies to polypropylene based materials that are widely used in hernia repair applications. Therefore, nano rough surface modification of such polymeric materials, as provided by the present invention, is a new paradigm for quick repair and surrounding tissue integration.

The present invention provides, in one aspect, a process for preparing a modified polymeric material using simultaneous heat and vacuum treatment on PEEK polymeric material (without chemical process) to create nano rough surface without compromising the mechanical, physical and chemical property of the polymer.

For polypropylene hernia meshes, the present invention provides, in one aspect, a method that uses a high vacuum source in the presence of pre-set mild heat or highly volatile methylene chloride treatment. The methylene chloride has a very low boiling point (less than 40° C.; close to body temperature heat) and can be removed spontaneously during the high vacuum treatment.

The present invention also relates to incorporating the process for preparing a modified polymeric material into the PEEK manufacturing process. This modified process can be useful for creating a surface or pores in polymers (such as when the polymer is molded/extruded for the first time).

The present invention also relates to using the process for preparing a modified polymeric material to surfaces that are already modified or will be modified thereafter. For example, the present invention contemplates using the modified process of the present invention to the top of a previously modified surface, and also contemplates using another method (e.g., acid etching) to further modify the modified surface after the process for preparing the modified polymeric material to the surface is completed.

EXAMPLES

The following examples are intended to illustrate particular embodiments of the present invention, but are by no means intended to limit the scope of the present invention.

Example 1

Nano PEEK Spine Cages

As provided by the present invention, research and testing has produced a nano surfaced PEEK without any chemical treatment, but using high vacuum (in the range of $10^{-2}$ Torr to $10^{-6}$ Torr) and a temperature of 350° C. at 15 min, 30 min, 60 min. The surface is novel and the processing method is novel.

Figure 2:
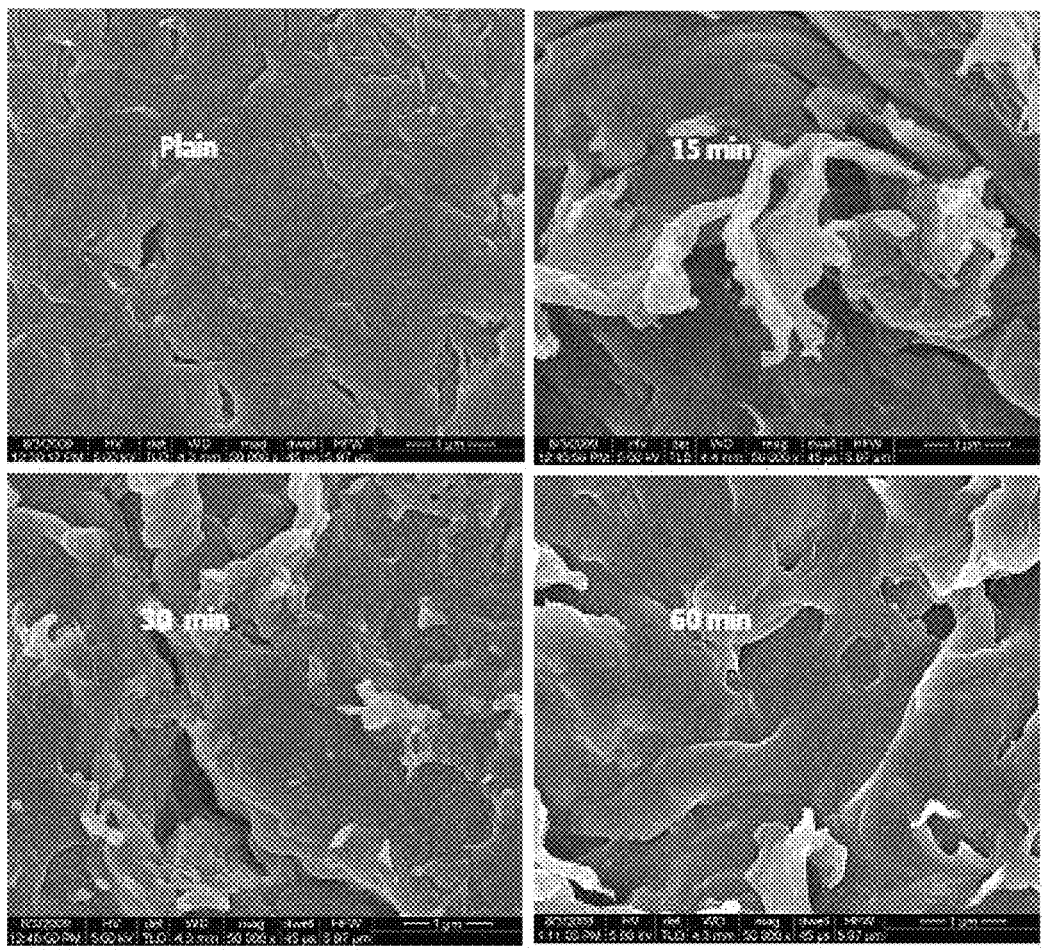
FIG. 2 are SEM images of the surface of PEEK (plain) and of the surface of modified nano PEEK after treatment using one embodiment of the process of the present invention.
Figure 3:
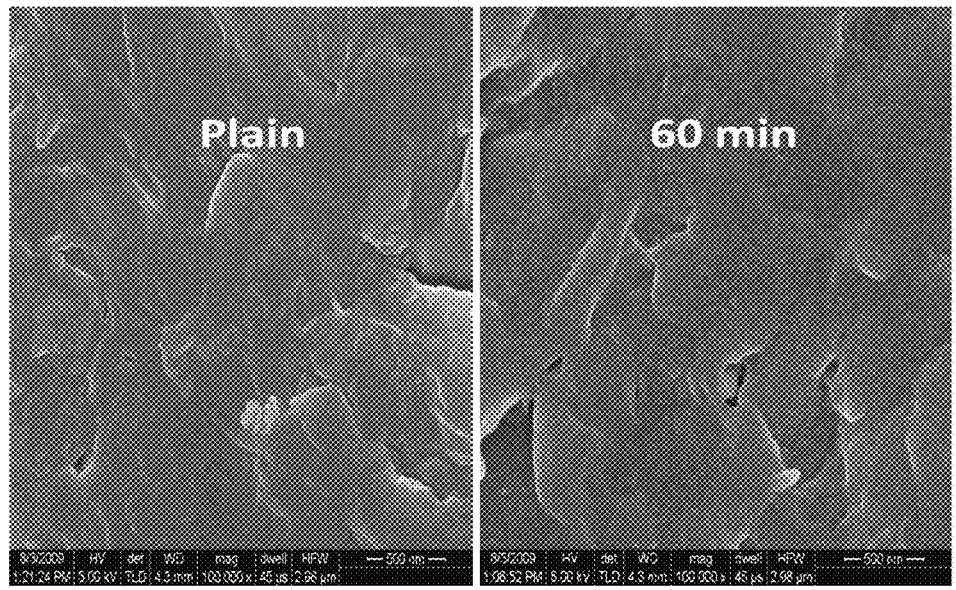
FIG. 3 are high magnification SEM images of the surface of PEEK (plain) and of the surface of a modified nano PEEK of the present invention.
Figure 4:
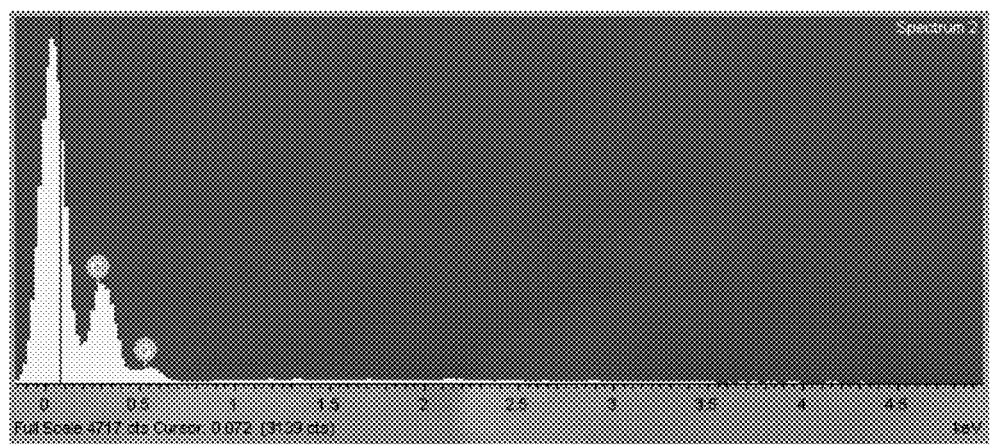
FIG. 4 is an EDS spectra of nano and conventional PEEK.

FIG. 1 is a schematic of one embodiment of the nano PEEK preparation method of the present invention. For example, PEEK coupons were kept in the pre-heated (at 350° C.) heating oven for 15, 30, 60 min, respectively. Ceramic plates were used to keep the coupons. After the above prescribed times, the samples were immediately transferred to a vacuum chamber and high vacuum was applied for 8 hours. Vacuum was released slowly and the PEEK samples were characterized further. SEM analysis (see FIGS. 2-3) and contact angle analysis experiments were performed and confirmed the nano features on the modified surfaces and changed contact angle values. Initial in vitro osteoblast cell data provided information that increased cell function on samples treated at 60 min compared to other timing points and plain PEEK samples. EDS spectra data was plain and nano PEEK samples (see FIG. 4). EDS data revealed that PEEK surface before and after treatment showed the same spectrum, indicating that there is no change in chemistry by the nano treatment process.

Figure 5:
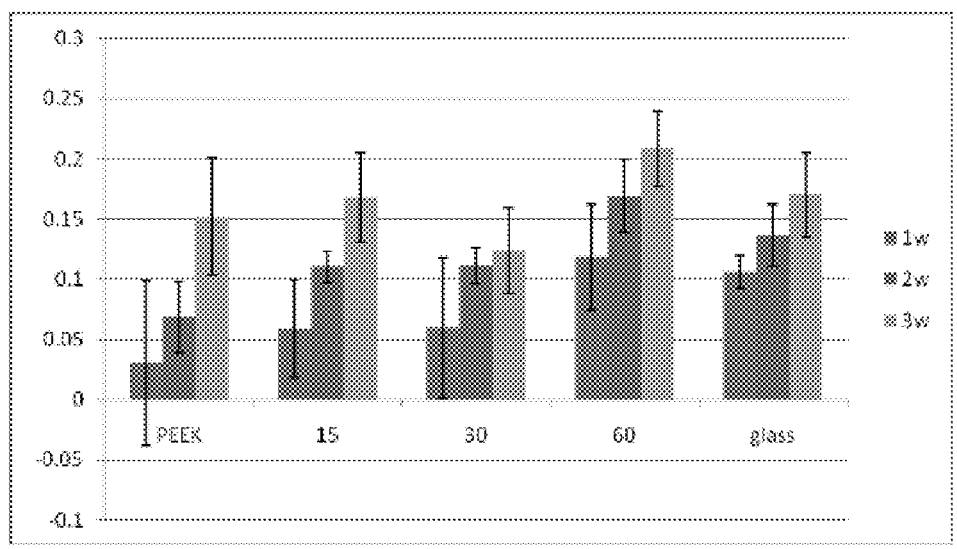
FIG. 5 is a bar graph showing heat-plus-vacuum treated PEEK calcium deposition data with osteoblast cells.

Calcium deposition studies with osteoblast cell showed that treated PEEK displayed significantly higher calcium after 1 w, 2 w, and 3 w, although percentage of increase decreased with time (see FIG. 5).

Example 2

Nano Polypropylene Hernia Mesh

As provided by the present invention, research and testing has produced two different novel nano surfaced polypropylene based hernia mesh scaffolds without any harsh chemicals (acids and bases). For example, one approach used mild, easily removable methylene chloride in combination with high vacuum (in the range of $10^{-2}$ Torr to $10^{-6}$ Torr). Additionally, a second nanorough surface was produced on the polymer scaffolds at the same high vacuum condition using a temperature of 60° C. without any chemical treatment. Both surfaces are novel and the processing methods are novel.

The surface of the polymer scaffold is processed at high vacuum (typically around at $10^{-6}$ Torr) with pre-set mild heat (at 60° C.) or with methylene chloride treatment without heat treatment for 24 hours (see FIG. 6). For the treated samples, polymer scaffolds were gradually brought down to atmospheric pressure and temperature.

To look for the surface difference between the samples due to the process illustrated in the depiction, Scanning Electron Microscope (SEM) images were obtained using FEI NOVA nanoSEM FESEM (FEI, Hillsboro, Oreg.) using low/high vacuum using through the lens (TLD) secondary electron detector using low to high magnification (10-200 k). Polymer scaffolds were mounted on copper tape using silver paste for additional conductivity. They were coated with Pt for 60 sec prior to imaging.

Accumulated charge from the electron beam was a problem but was reduced due to the better conductivity provided by embedding the mesh in silver paste.

Figure 7A:
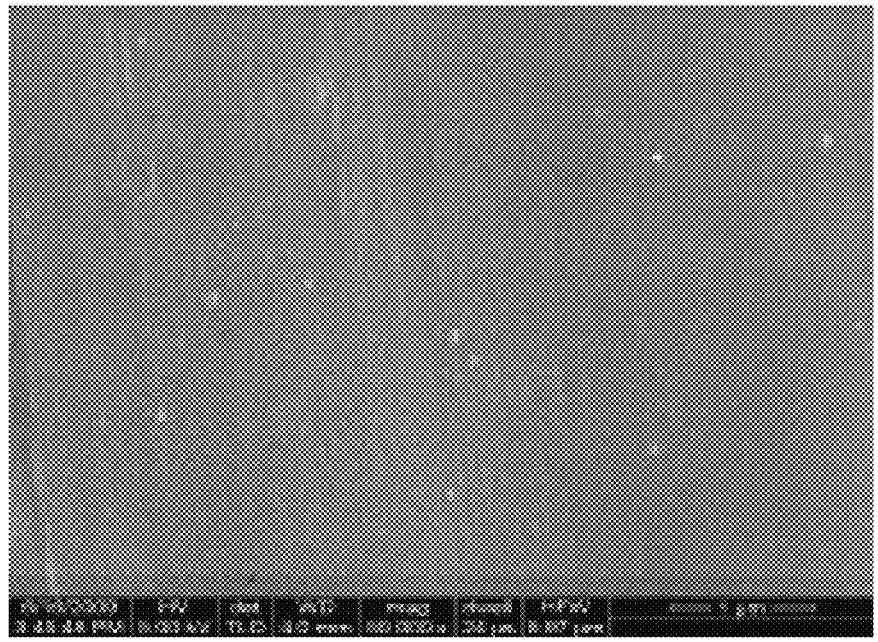
FIGS. 7A-7C are SEM images of a polypropylene mesh (plain) (FIG. 7A) and of polyproplyene meshes of the present invention having various nano features.
Figure 7B:
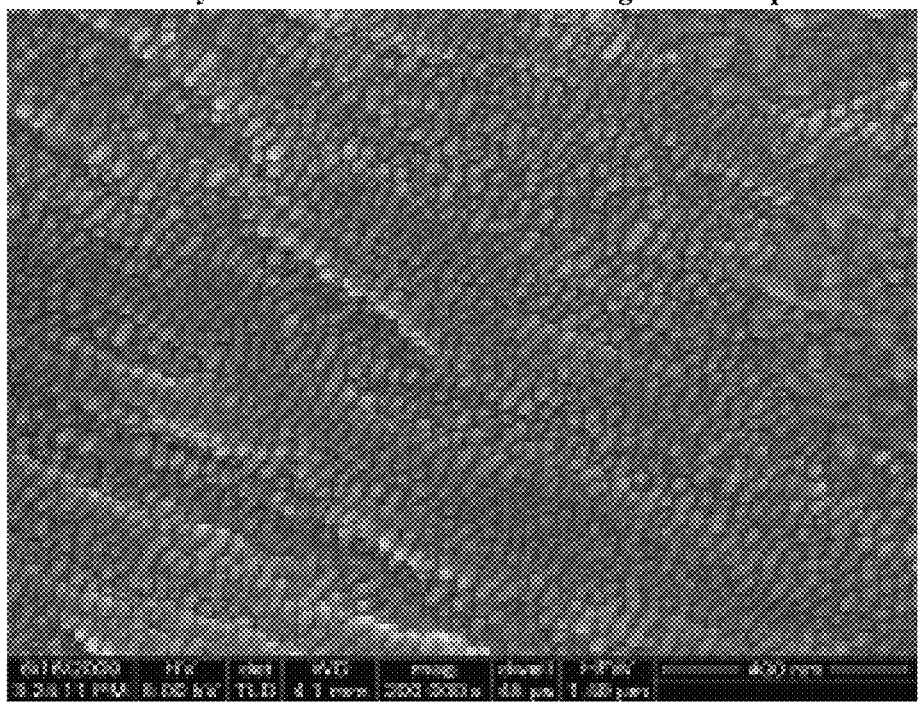
Figure 7C:
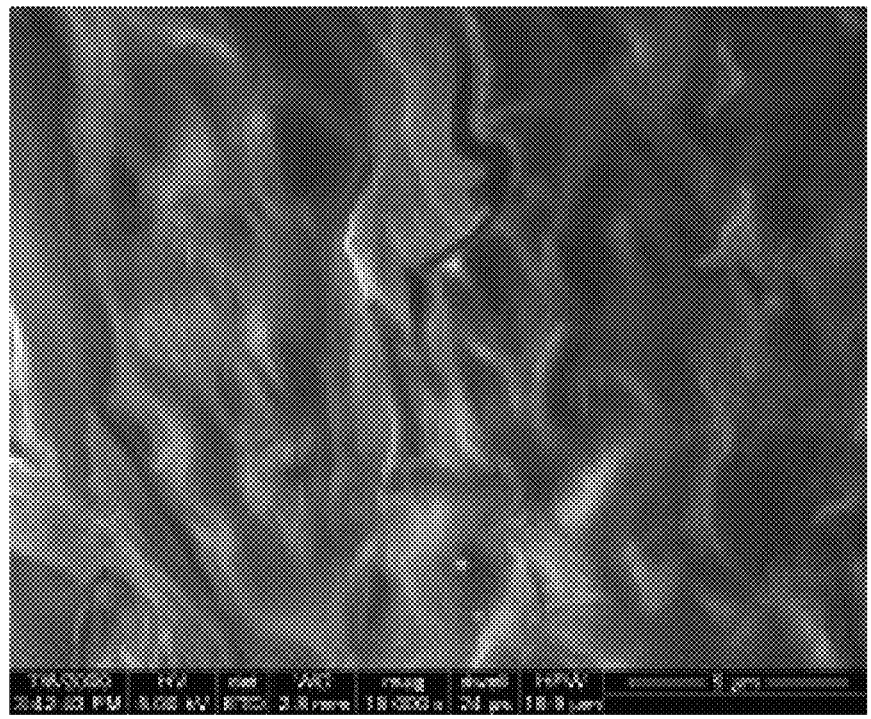

Fine nano surface features were evident under above SEM condition for treated samples compared plain samples (see FIG. 7). The difference in the nanorough pattern reflects the two different processes used with same polymer scaffold.

Therefore, the present invention is effective to produce at least two different nanoroughness patterns on the same polymer using a high vacuum process with pre-set mild heat treatment and with methylyne chloride treatment.

Example 3

Calcium Deposition Results Using Osteoblast Cells

Calcium deposition studies with osteoblast cells were conducted for various embodiments of the process of preparing modified polymeric materials having micron and submicron surface roughness. In particular, calcium deposition studies were conducted using PEEK nanosurfaced using (i) a sulfuric acid etching technique (PEEK 1) and (ii) a heat plus high vacuum technique (PEEK 2), as described herein.

Figure 8:
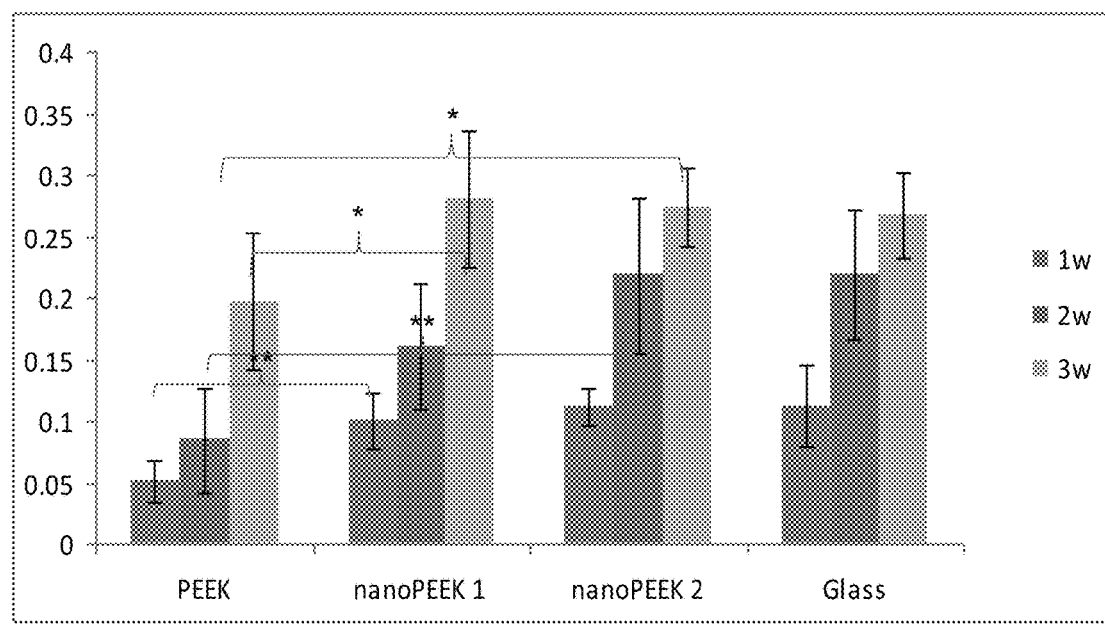
FIG. 8 is a bar graph showing calcium deposition data with osteoblast cells for PEEK (untreated), nanoPEEK 1 ($H_2SO_4$ treated), and nanoPEEK 2 (heated at 350° C. for 1 hour followed by vacuum) after 1 week, 2 weeks, and 3 weeks.
Figures 9A, 9B:
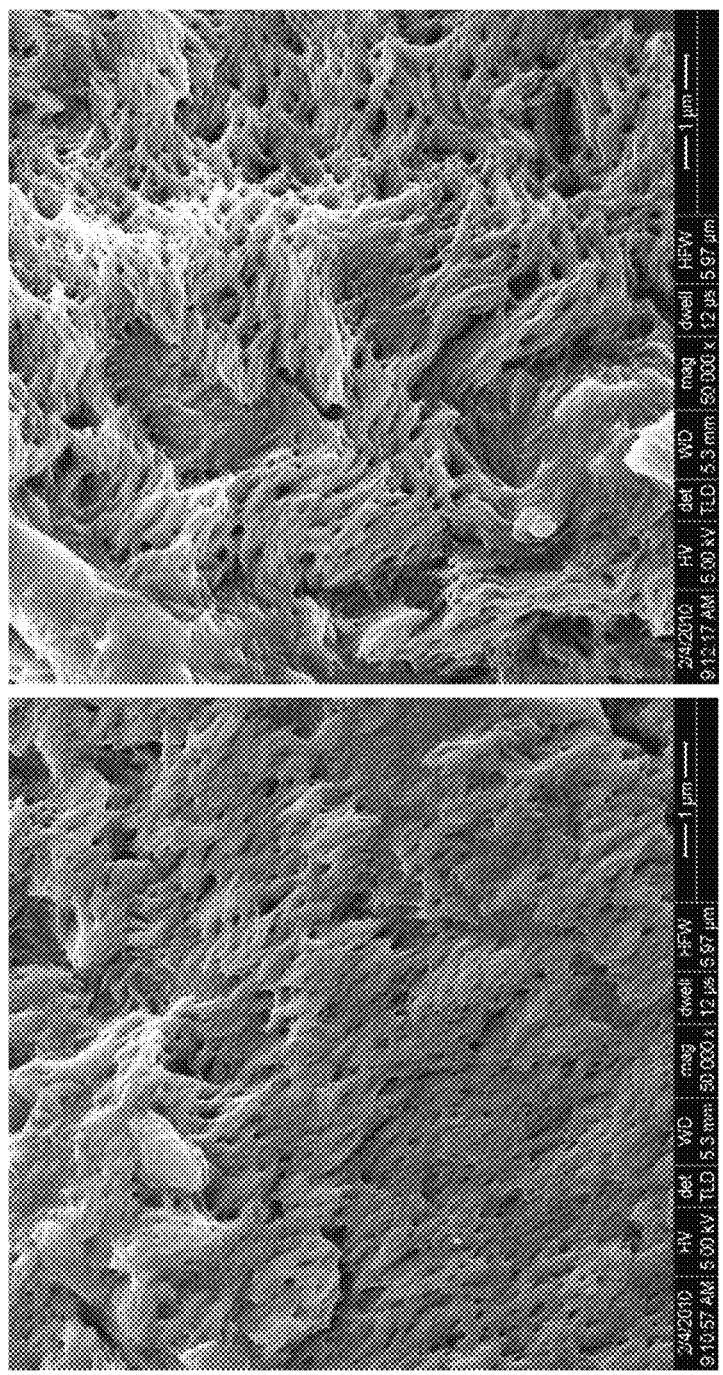
FIGS. 9A-9B are SEM images of the surface of modified nano PEEK materials produced according to one embodiment of the process of preparing a modified polymeric material of the present invention.
Figures 10A, 10B:
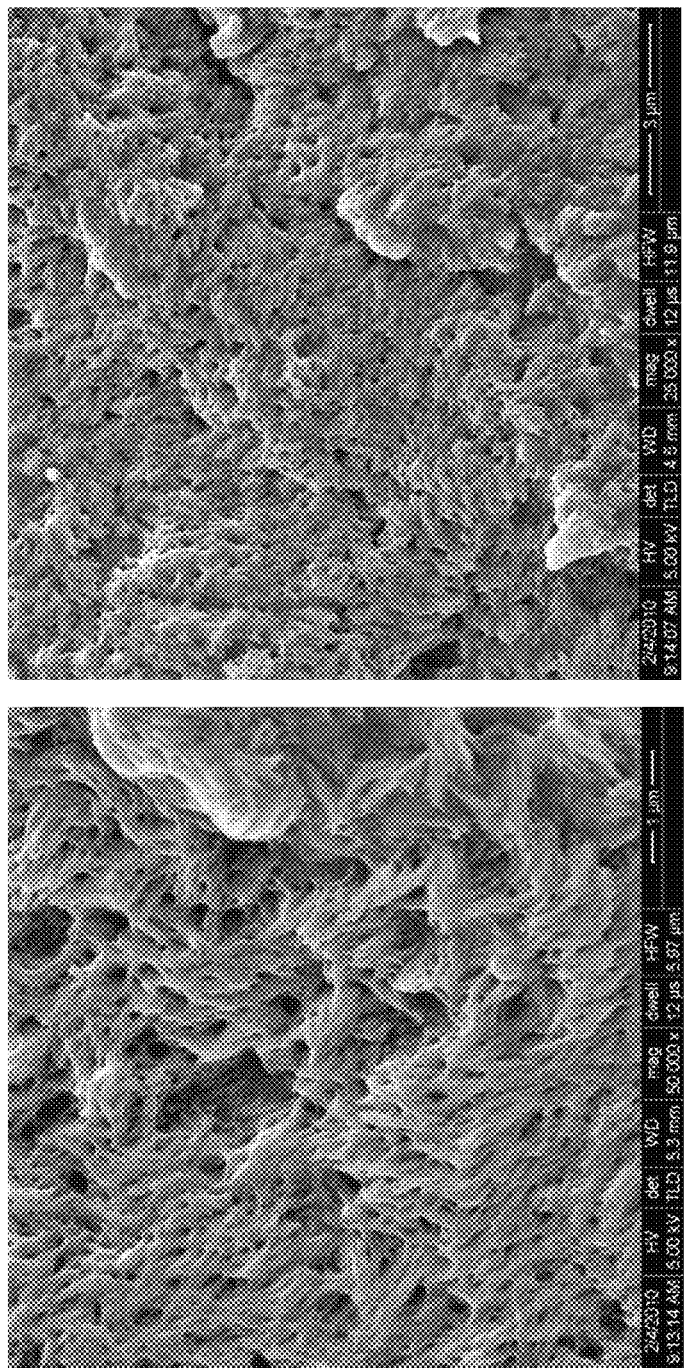
FIGS. 10A-10B are SEM images of the surface of modified nano PEEK materials produced according to one embodiment of the process of preparing a modified polymeric material of the present invention.
Figure 11B:
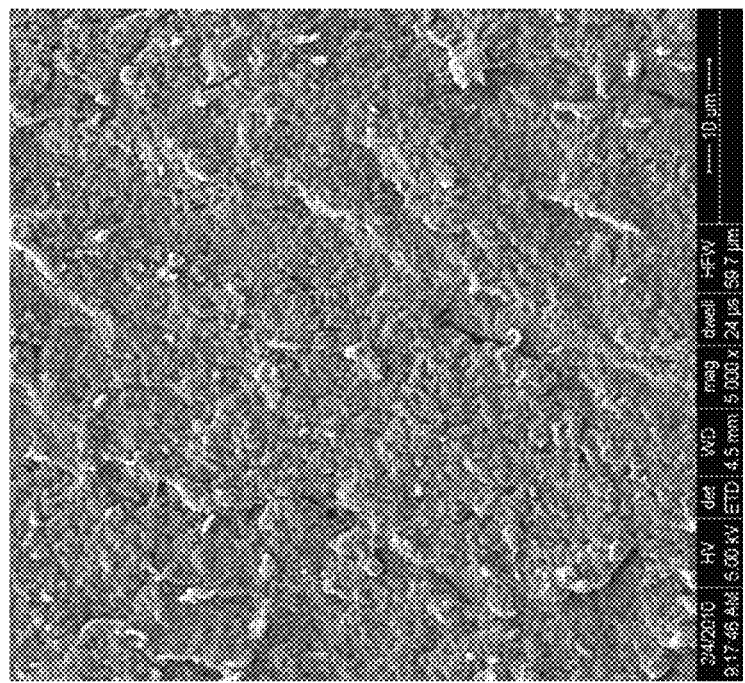
FIGS. 11A-11B are SEM images of the surface of modified nano PEEK materials produced according to one embodiment of the process of preparing a modified polymeric material of the present invention.
Figure 11A:
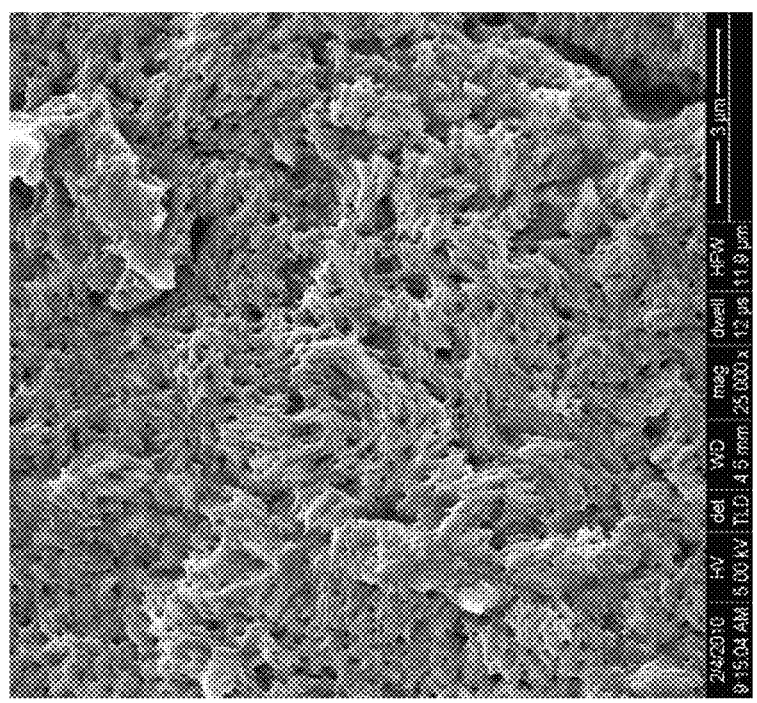
Figure 12:
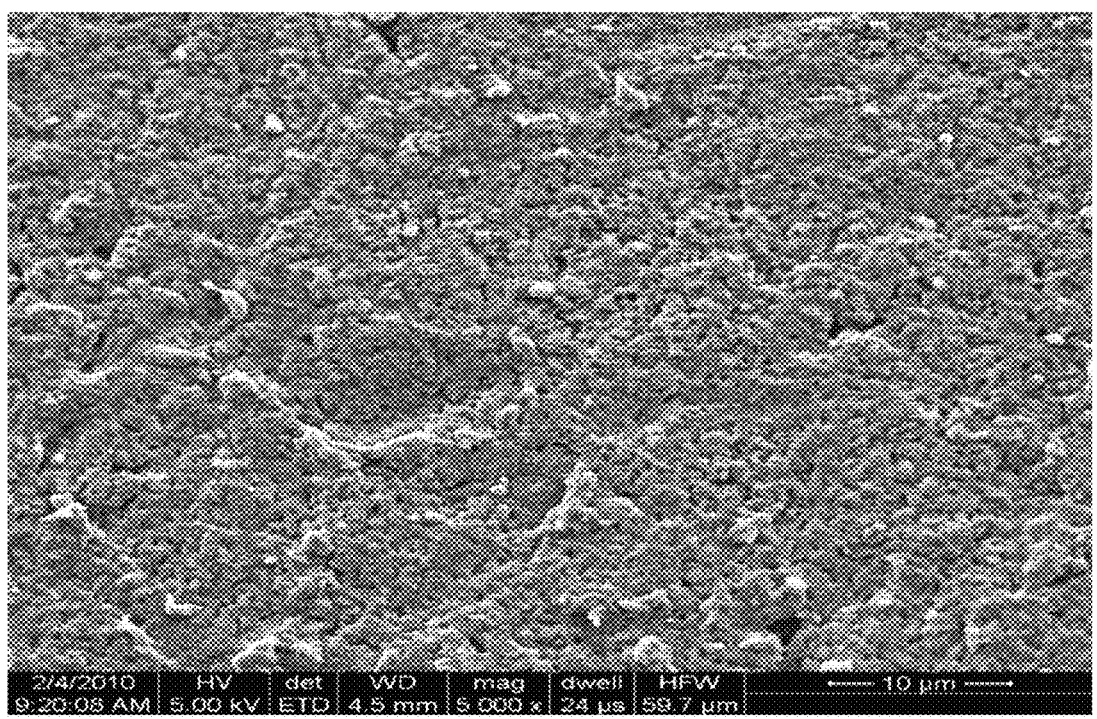
FIG. 12 is an SEM image of the surface of a modified nano PEEK material produced according to one embodiment of the process of preparing a modified polymeric material of the present invention.

FIG. 8 illustrates the calcium deposition/osteoblast cell results PEEK (untreated), nanoPEEK 1 ($H_2SO_4$ treated), nanoPEEK 2 (heated at 350° C. for 1 hour, followed by vacuum), and glass after 1 w, 2 w, and 3 w.

Increased osteoblast adhesion correlates to enhanced cell-to-cell contact which can promote osteoblast differentiation to calcium depositing cells. Compared to untreated PEEK, this study provided evidence of enhanced Ca deposition on both treated PEEK after 3 weeks. While Ca deposition by both treated PEEK was not different from glass surface, it was significantly greater compared to plain PEEK surface. There are many possible reasons why Ca deposition may be enhanced on these nano PEEK materials, particularly with the invented nano-featured surfaces. Specifically, compared to plain PEEK materials, nano PEEK materials have greater surface areas and consequently higher numbers of atoms at their surfaces.

Example 4

Nanosurfacing of Polymers Using Heat with Simultaneous Vacuum

As discussed elsewhere herein, in one aspect, the present invention relates to a process for preparing a modified polymeric material. Research was conducted on a particular embodiment of this process (described below), where the process generally involved subjecting polymers (targeted for nanosurfacing) to heat with simultaneous vacuum.

In this example, the high vacuum treatment regimen included loading polymer samples (i.e., PEEK) at 150° C. and subjecting the polymer to pump-down procedures to 10 mTorr (pump/purge sequences). Thereafter, the polymer was subjected to a ramp-up period during which the temperature was increased from about 150° C. to about 350° C. over the course of approximately 1 hour. The polymer was left at steady state for about 1 hour (at 10 mTorr at 350° C.). The polymer was then subjected to a ramp-down period during which the temperature was decreased to about 150° C. over the course of 1 hour. The sample was then extracted at 150° C. and transferred to a vacuum desiccator and stored under high vacuum for approximately 8 hours.

Figure 13:
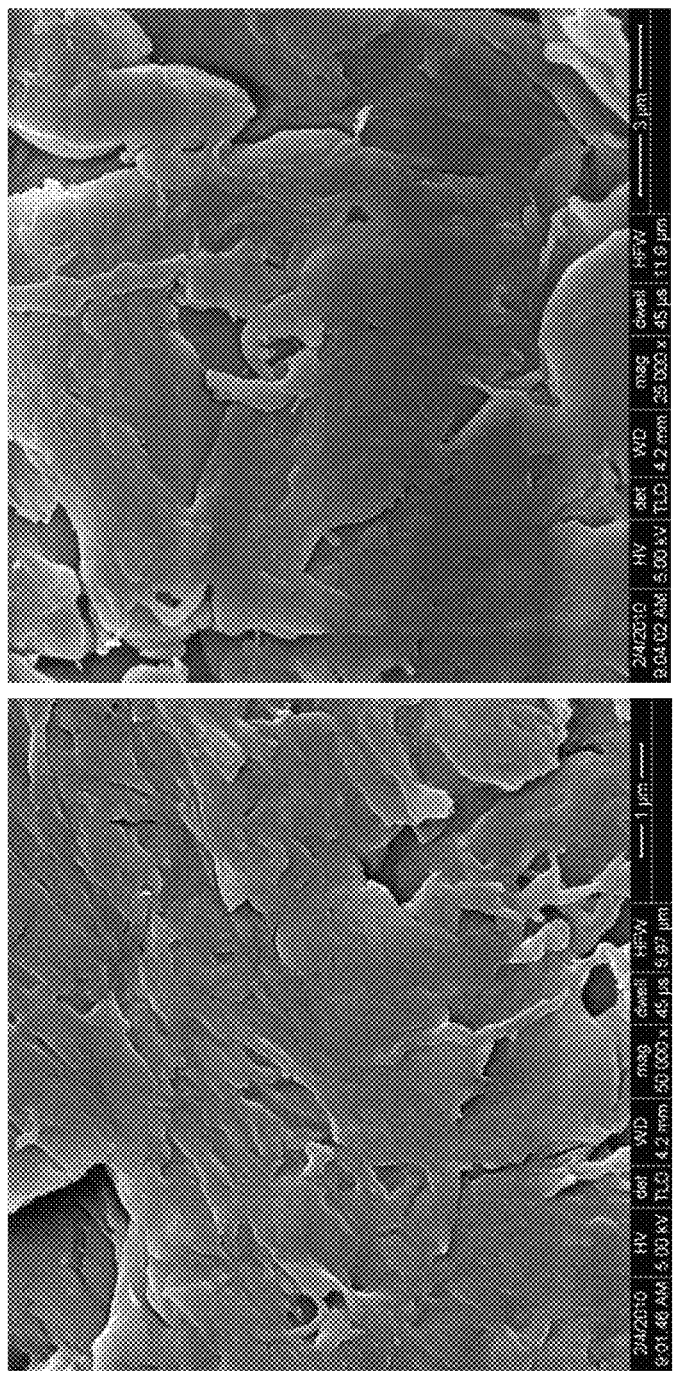
FIGS. 13A-13B are SEM images of the surface of non-modified PEEK materials.
Figure 14:
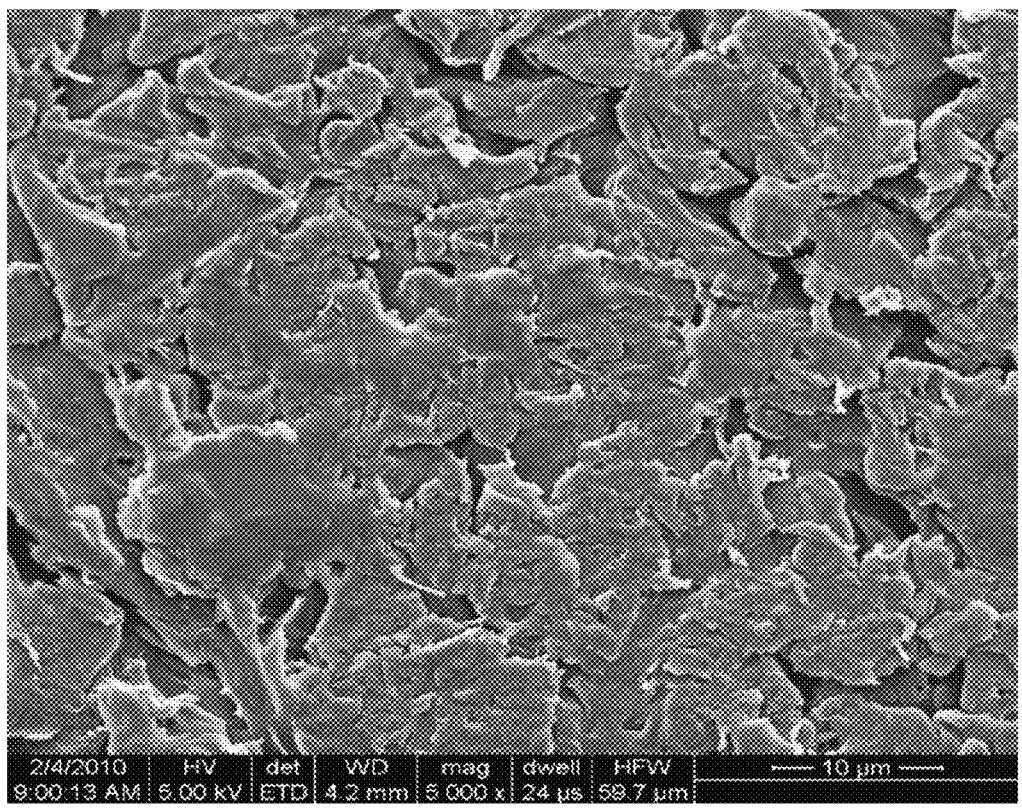
FIG. 14 is an SEM image of the surface of a non-modified PEEK material.

Results of the polymer nanosurfaces produced by this process are shown in the SEM images of FIGS. 9-12 and 15, as compared to "plain" polymer surfaces as shown in the SEM images of FIGS. 13-14.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A process for preparing a modified polymeric material, said process comprising:
   providing a polymer, wherein the polymer is polyetheretherketone (PEEK); and
   subjecting the polymer to a high vacuum treatment regimen under conditions effective to modify a surface of the polymer by introducing to the surface of the polymer features selected from the group consisting of nanoscale features, micron scale features, and submicron scale features,
   wherein said high vacuum treatment regimen comprises simultaneously heating the polymer at a temperature of between 275° C. and 400° C. and incubating the polymer in a vacuum chamber under high vacuum conditions in a range of $10^{-2}$ Torr to $10^{-6}$ Torr effective to modify the surface of the polymer,
   wherein said subjecting comprises:
   (a) loading the polymer at a first temperature;
   (b) increasing the temperature during a ramp-up period to a second temperature of 275° C. to 400° C.;
   (c) maintaining the polymer at the second temperature;
   (d) then, decreasing the temperature by 125° C. to 250° C. during a ramp-down period to a third temperature; and
   (e) after the ramp-down period, extracting the polymer.

2. The process according to claim 1, wherein the first temperature is about 150° C.

3. The process according to claim 1, wherein the second temperature is about 275° C. to about 350° C.

4. The process according to claim 1, wherein the third temperature is about 150° C.

5. The process according to claim 1, wherein the ramp-up period is performed over the course of about 1 hour.

6. The process according to claim 1, wherein the polymer is maintained at the second temperature for about 1 hour.

7. The process according to claim 1, wherein the ramp-down period is performed over the course of about 1 hour.

8. The process according to claim 1, wherein said incubating is carried out for at least 5 hours.

9. The process according to claim 1, further comprising storing the extracted polymer under high vacuum conditions in a range of $10^{-2}$ Torr to $10^{-6}$ Torr for about 8 hours.

10. The process according to claim 1, further comprising at least one of:
    applying an acid etching procedure either before or after the polymer is modified; and
    integrating or coating the modified polymeric material with another material to yield a two layer or integration of the modified polymeric material and the other material.

11. The process according to claim 10, wherein the other material comprises hydroxyapatite, titanium, or calcium.

12. The process according to claim 1, wherein the polymer is in the form of a polymeric film, fiber, sphere, ovoid, rod, filament, monofilament, or scaffold, plug, or matrix.

13. The process according to claim 1, wherein said modified polymeric material is effective to modify a biological response, fixation, or a therapeutic attachment/delivery compared to a corresponding non-modified polymeric material.

14. The process according to claim 13, wherein said modified polymeric material is effective to modify the biological response, and the biological response is selected from the group consisting of protein or antibody adsorption, cell attachment, cell function, and tissue growth.

15. The process according to claim 13, wherein said modified polymeric material is effective to modify the therapeutic attachment/delivery, and the therapeutic is selected from the group consisting of a peptide, protein, growth factor, antibody, drug, metal, antimicrobial metal, antibiotic metal, biologic tissue, biologic agent, chemical agent, stem cell, and modified cell.

16. The process according to claim 1, wherein the modified polymeric material further comprises at least one of:
 a functional attachment effective to increase biological response or therapeutic attachment/delivery; and
 a ceramic, metal, or another polymer integrated into the modified polymeric material or coated onto the surface of the modified polymeric material.

17. The process according to claim 16, wherein the functional attachment is selected from the group consisting of a peptide, protein, growth factor, antibody, drug, metal, antimicrobial metal, antibiotic metal, biologic tissue, biologic agent, chemical agent, stem cell, and modified cell.

18. A process for making an implant, said process comprising preparing a modified polymeric material according to claim 1, and forming an implant comprising the modified polymeric material.

19. The process according to claim 18, wherein the implant is a spine cage, vertebral body replacement, suture anchor, dental implant, or maxillofacial implant.

* * * * *